United States Patent
Lee et al.

(10) Patent No.: US 9,012,455 B2
(45) Date of Patent: Apr. 21, 2015

(54) PHARMACEUTICAL COMPOSITIONS CONTAINING AN INDOYL ISOQUINOLINE CONTAINING COMPOUND AND USES THEREOF

(75) Inventors: Wen-Hwa Lee, Newport Coast, CA (US); Phang-Lang Chen, Irvine, CA (US); Longen Zhou, Irvine, CA (US); Jiewen Zhu, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 1230 days.

(21) Appl. No.: 12/296,720

(22) PCT Filed: Apr. 10, 2007

(86) PCT No.: PCT/US2007/008969
§ 371 (c)(1),
(2), (4) Date: May 14, 2009

(87) PCT Pub. No.: WO2007/120726
PCT Pub. Date: Oct. 25, 2007

(65) Prior Publication Data
US 2009/0312324 A1     Dec. 17, 2009

Related U.S. Application Data

(60) Provisional application No. 60/791,545, filed on Apr. 11, 2006.

(51) Int. Cl.
*A61K 31/4725* (2006.01)
*A61K 31/506* (2006.01)
*A61K 31/4745* (2006.01)

(52) U.S. Cl.
CPC .................. *A61K 31/4745* (2013.01)

(58) Field of Classification Search
CPC ............................ C07D 401/04; C07D 401/14
See application file for complete search history.

(56) References Cited

FOREIGN PATENT DOCUMENTS

WO     2006/044933     4/2006

OTHER PUBLICATIONS

Roussidis, et al.; "STI571 as a potent inhibitor of growth and invasiveness of human epithelial breast cancer cells"; 2004; Anticancer Res.; 24(3a): 1445-7; PubMed abstract; PMID: 15274308.*
Aloyz et al.; "Imatinib sensitizes CLL lymphocytes to chlorambucil"; 2004; Leukemia; 18: 409-414.*
Slupianed, et al., "Fusion Tyrosine kinases Induce Drug Resistance by Stimulation of homology-Dependent Recombination Repair, Prolongation of G2/M Phase, and Protection from Apoptosis"; Molecular and Cellular Biology Jun. 2002, vol. 22, No. 12, pp. 4189-4201.

* cited by examiner

*Primary Examiner* — Timothy Thomas
(74) *Attorney, Agent, or Firm* — Fish & Tsang, LLP

(57) ABSTRACT

Chronic myelogenous leukemia (CML), and in particular imatinib resistant CML is treated using compositions and methods in which a Rad51-inhibitor and a kinase inhibitor are administered. Most preferably, the Rad51 inhibitor comprises an indolyl isoquinoline structure and the kinase inhibitor is a BCR-ABL inhibitor.

2 Claims, 8 Drawing Sheets

PHARMACEUTICAL COMPOSITIONS CONTAINING AN INDOYL ISOQUINOLINE CONTAINING COMPOUND AND USES THEREOF

This application claims priority to our U.S. provisional patent application with the Ser. No. 60/791,545, which was filed Apr. 11, 2006, and which is incorporated by reference herein.

This invention was made with government support from the Department of Defense with grant number DAMD 17-02-1-0694. The government may have certain rights in the invention.

FIELD OF THE INVENTION

The field of the invention is pharmaceutical compositions and methods for treatment of imatinib resistant chronic myelogenous leukemia (CML).

BACKGROUND OF THE INVENTION

One characteristic parameter of cancer cells is their higher than normal fraction of cells in S-phase. Thus, various attempts have been made to develop "S-phase specific" anticancer drugs. For example, Camptothecin, which is a topoisomerase I inhibitor, showed S-phase specific cytotoxicity.

Another equally essential biochemical event for DNA replication during S-phase is homologous recombination (HR), which is used to restart the collapsed or stalled replication fork. When double-stranded DNA breaks occur at G1 or M phase of mammalian cells, non-homologous end joining (NHEJ) plays a major role in repairing those breaks. One possibility to explain this discrepancy lies in the presence of required factors for HR in S phase. Among a number of genes critical for HR in eukaryotes, Rad51 recombinase plays a quintessential role. Rad51 multimerizes to form a nucleoprotein filament on single-stranded DNA and catalyzes homologous DNA pairing and strand exchange in vitro. After treatment with DNA damaging agents, Rad51 foci can be observed at the sites of DNA lesion along with other HR-related proteins such as BRCA1, BRCA2, BLM and RPA. In many cancer cells, enhanced HR and increased expression of Rad51 have been observed, while in normal cells, Rad51 expression is restricted to S phase and the recombination frequency and its expression level are much lower than those in cancer cells. Moreover, Rad51 is positively correlated with resistance of cancer cells to DNA damage inducing radio- or chemotherapies, which suggests that elevated levels of Rad51 in the HR pathway are critical for the proliferation of cancer cells rather than normal somatic cells.

Rad51 is also a key effector downstream of BCR-ABL, essential for cell proliferation and survival. Bcr/Abl, a constitutively active fusion tyrosine kinase derived from Philadelphia chromosome (t9:22), is found in most (95%) chronic myelogenous leukemia (CML) and in many acute lymphocytic leukemia (ALL) patient. Bcr/Abl-expressing cells are typically resistant to genotoxic treatments, and it has been shown that Bcr/Abl-Stat5-Rad51 pathway in leukemia cells stimulates homologous recombination (HR), contributing to the resistance to DNA damaging agents. In BCR-ABL positive leukemia cells, Rad51, itself a direct substrate of BCR-ABL, is transcriptionally activated via BCR-ABL-Stat5 pathway. Because of the constitutive activation of BCR-ABL, Rad51 protein level is constantly elevated in these cells, contributing to resistance to chemotherapies and the continuous cell proliferation.

The elevation of Rad51 levels in CML is a major downstream event of Bcr-Abl regulation and contributes to the proliferation and drug resistance of CML cells. Current therapeutics, such as Imatinib treatment, have proven to be successful in the inhibition of BCR-ABL activity, but suffer from relapse after developing new resistance to the drug. Unfortunately, resistance to imatinib occurs frequently (over 70%) in accelerated phase (AP) and myeloid blast crisis (BC) patients, resulting in remissions lasting for only 6-12 months. The major mechanism of acquired resistance to imatinib is mutations in BCR-ABL kinase domain. One of the most serious mutations is T315I, which is responsible for about 15% of imatinib-resistant CML cases. The T315I mutation also confers resistance to dasatinib (BMS-354825) and nilotinib (AMN107), two second generation BCR-ABL inhibitors, which were developed to overcome imatinib-resistance. In addition, resistance to imatinib can also be caused by mutations located outside the kinase domain, which are most likely beyond the scope of more specific BCR-ABL kinase inhibitors. For that reason, developing new approaches to circumvent or counteract resistance to BCR-ABL kinase inhibitors still poses a challenging problem, especially in late phase CML.

Therefore, while there are various drugs and conceptual drug therapies known in the art, successful implementation is often prevented by development of resistance, or by lack of functional and/or well-tolerated drug candidates. Thus, there is still a need to provide new therapeutic agents to treat CML, and especially treatment resistant CML.

SUMMARY OF THE INVENTION

The present invention is directed to compositions and methods of treatment of various neoplastic diseases, more particularly CML, and especially imatinib resistant CML. In most preferred aspects, treatment comprises coadministration of a BCR-ABL tyrosine kinase inhibitor with compounds that interfere with RAD51 multimerization or association with other RAD51 ligands.

In one aspect of the inventive subject matter, a pharmaceutical composition comprises in a pharmaceutically acceptable carrier a kinase inhibitor (preferably a BCR-ABL kinase inhibitor, and most preferably imatinib, dasatinib, nilotinib, tyrphostin, an adamantyl ester of tyrphostin, AMN107, and/or BMS-354825) and a compound according to Formula 1, respectively

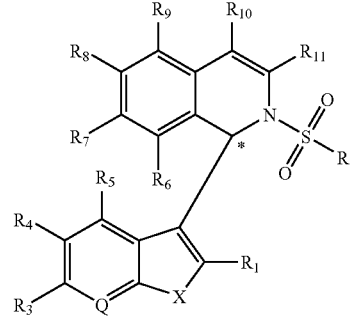

Formula 1 wherein R is a radical selected from the group consisting of an alkyl, alkenyl, alkynyl, cycloalkyl, cycloalkenyl, alkaryl, and

wherein Y is null or an alkylene group having 1 to 4 carbon atoms; Z is selected from —C(R$_{12}$)═C(R$_{13}$)—, —CH═N—, —N═CH—, O, S, or NR$_{14}$, where R$_{14}$ is H, alkyl, aryl, aralkyl, or acyl; Q is N or C—R$_2$; X is selected from CH$_2$, O, S, or NR$_{14}$, where R$_{14}$ is independently as defined above; R' and R$_1$ through R$_{13}$ are independently selected from the group consisting of H, or optionally substituted alkyl, alkenyl, alkynyl, cycloalkyl, cycloalkenyl, halo, nitro, hydroxy, alkoxy, alkenyloxy, cyano, carboxy, alkoxycarbonyl, carboxyalkyl, amino, acylamino, alkylamino, dialkylamino, cycloalkylamino, morpholino, N-alkyl, N-cycloalkyl, amino, thio, alkylthio, and haloalkyl; with the proviso that R$_{12}$ and R$_{13}$ optionally combine to form a carbocyclic or heterocyclic ring; wherein each of R' and R$_1$ through R$_{13}$ optionally independently includes a solubilizing group; and wherein n is between 0 and 4, inclusive, and * denotes R or S configuration (racemic mixtures are also contemplated). Typically, both the kinase inhibitor and the compound are present in an amount effective to treat imatinib-resistant CML.

More preferably, R$_1$ through R$_{11}$ are independently H or a solubilizing group, wherein X is NR$_{14}$, and wherein R is

and most preferably, Z in such compounds is —C(R$_{12}$)═C(R$_{13}$)—, and Y is null. Therefore, and among other suitable choices, the compound has a structure of Formula 1A, 1B, or 1C

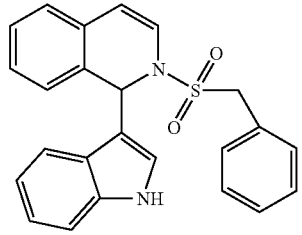

Formula 1A

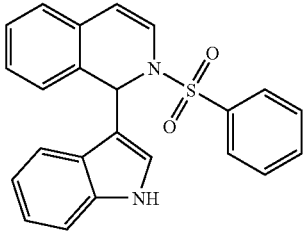

Formula 1B

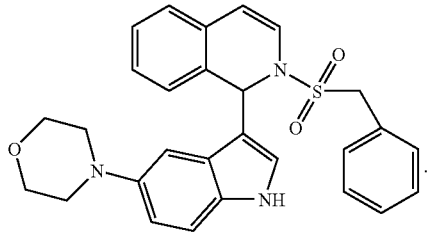

Formula 1C

In another aspect of the inventive subject matter, a method of facilitating treatment of CML comprises a step of advising that administration of a kinase inhibitor and a compound according to claim 1 is effective to treat CML, wherein the step of advising may include instructing a physician to co-administer the kinase inhibitor and the compound, providing a regulatory filing with information to co-administer the kinase inhibitor and the compound, or selling together the kinase inhibitor and the compound to patient. In especially preferred aspects of such methods, CML is imatinib-resistant CML, the kinase inhibitor is a BCR-ABL inhibitor, and/or the compound is a compound as described above.

Consequently, and viewed from yet another different perspective, the inventors also contemplate use of a compound according to claim 1 in the manufacture of a medicament to treat CML, wherein the CML is concurrently treated with a kinase inhibitor. Preferably, the CML is imatinib resistant, the compound is a compound as described above, and the kinase inhibitor is a BCR-ABL inhibitor (e.g., imatinib, dasatinib, nilotinib, tyrphostin, an adamantyl ester of tyrphostin, AMN107; and BMS-354825).

Various objects, features, aspects and advantages of the present invention will become more apparent from the following detailed description of preferred embodiments of the invention.

DETAILED DESCRIPTION

Figure 1:
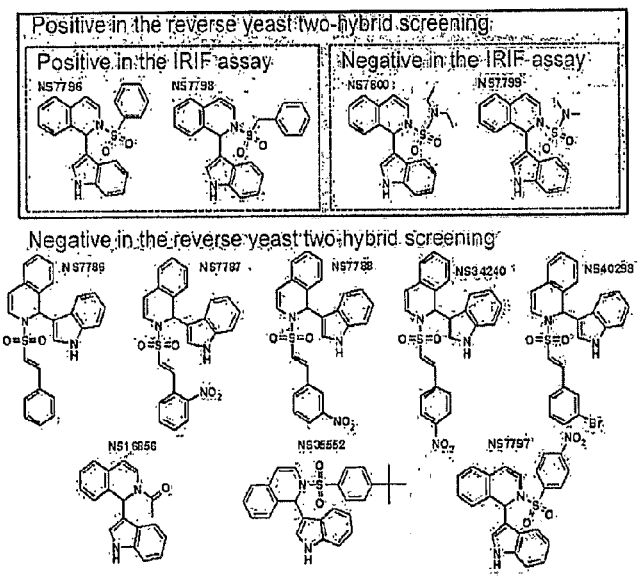
FIG. 1A depicts exemplary compounds selected from the yeast two-hybrid screening assay and selected SAR results.
FIG. 1B is the structure of IBR2 with a chiral center indicated by *.
FIG. 1C is an exemplary chromatogram of chiral separation of R- and S-isomers of IBR2.
FIG. 1D depicts exemplary results for binding of a racemic mixture, and R- and S-isomers of IBR2 in vitro.
Figure 1:
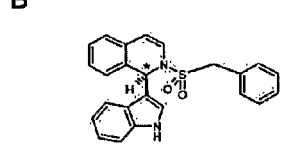
Figure 1:
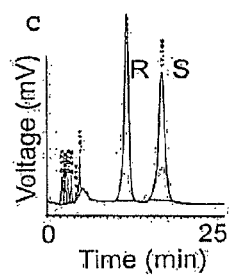
Figure 1:
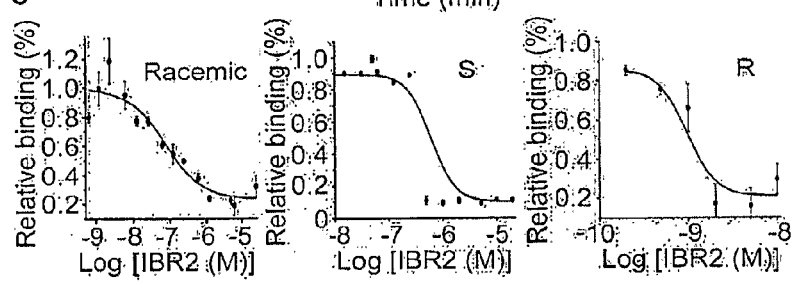

The inventors have surprisingly discovered that various small molecule drugs can be prepared (e.g., IBR2) that mimic the N-terminal architecture of Rad51, competitively inhibit BRC-repeat binding, and inhibit ATP-dependent multimerization of Rad51 in vitro.

Most significantly, synergistic effects between such inhibitors and BCR-ABL kinase inhibitors were observed in the treatment of cells expressing wild-type BCR-ABL. Moreover, in cells expressing imatinib-resistant mutants, including T315I, IBR2 treatment alone induced apoptosis in culture and significantly prolonged animal survival. Remarkably, treatment with two inhibitors (e.g., imatinib and IBR2) targeting two distinct mechanisms (i.e., kinase and RAD51 association) showed synergistic effect in the human blast crisis cell line K562. Thus, it should be particularly appreciated that IBR2 alone or in combination with a BCR-ABL kinase inhibitor may provide a new and promising route of treatment for imatinib-resistant cells or late stage CML patients.

Contemplated Compounds and Compositions

Based on numerous experiments and structure-activity data (not shown), additional compounds suitable for use in conjunction with the teachings presented herein include the following compounds according to Formula I:

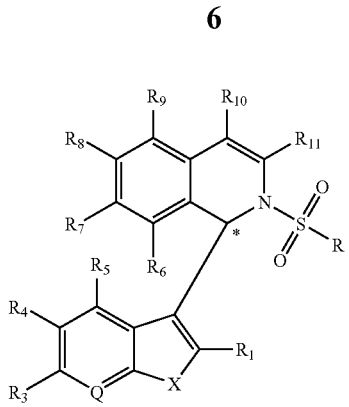

Formula 1 wherein R is an optionally substituted radical selected from the group consisting of an alkyl, alkenyl, alkynyl, cycloalkyl, cycloalkenyl, alkaryl, and

wherein Y is null or an optionally substituted alkylene group having 1 to 4 carbon atoms (in which case R is most preferably bound to the sulfur atom via a carbon atom of Y), Z is —C($R_{12}$)=C($R_{13}$)—, —CH=N—, —N=CH—, O, S, or $NR_{14}$, where $R_{14}$ is H, alkyl, aryl, aralkyl, or acyl, Q is N or C—$R_2$, X is selected from $CH_2$, O, S, or $NR_{14}$, where $R_{14}$ is independently as defined above, R' and $R_1$ through $R_{13}$ are independently selected from the group consisting of H, optionally substituted alkyl, alkenyl, alkynyl, cycloalkyl, cycloalkenyl, halo, nitro, hydroxy, alkoxy, alkenyloxy, cyano, carboxy, alkoxycarbonyl, carboxyalkyl, amino, acylamino, alkylamino, dialkylamino, cycloalkylamino, morpholino, N-alkyl, N-cycloalkyl, amino, thio, alkylthio, and haloalkyl; R' and $R_1$ through $R_{13}$ may further independently include a solubilizing group, which may or may not be cleavable within a cell; moreover, $R_{12}$ and $R_{13}$ optionally combine to form a carbocyclic or heterocyclic ring, n is between 0 and 4, inclusive, and * denotes R or S configuration.

Therefore, and among other contemplated compounds, especially suitable compounds include those according to Formula 1A (IBR2), 1B (IBR1), and 1C below:

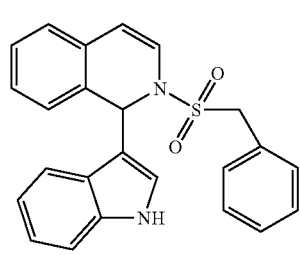

Formula 1A

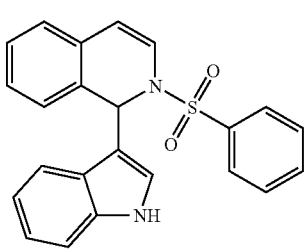

Formula 1B

-continued

Formula 1C

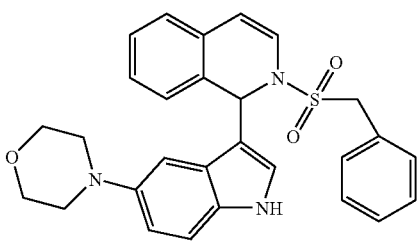

Of course, it should be appreciated that all contemplated compounds may be optically pure, or mixtures of optical isomers. Furthermore, all enantiomers, tautomers, and other isomeric forms are contemplated herein. Additionally, it is contemplated that the compounds according to the inventive subject matter may also be present in form of a prodrug, a metabolite, and/or a salt with a pharmaceutically acceptable acid or base.

The term "alkyl" as used herein refers to a cyclic, branched, or straight hydrocarbon in which all of the carbon-carbon bonds are single bonds, and the term "lower alkyl" refers to a cyclic, branched, or straight chain alkyl of one to ten carbon atoms (e.g., methyl, ethyl, n-propyl, i-propyl, n-butyl, t-butyl, i-butyl (or 2-methylpropyl), cyclopropylmethyl, i-amyl, n-amyl, hexyl, etc.). The term "alkylene" as used herein refers to an alkyl having two hydrogen atoms less than the corresponding alkane (i.e., $C_nH_{2n}$). For example, suitable alkylenes include methylene groups, ethylene groups, propylene groups, etc. The term "cycloalkyl" as used herein refers to a cyclic or polycyclic alkyl group containing 3 to 15 carbons. For polycyclic groups, these may be multiple condensed rings in which one of the distal rings may be aromatic (e.g., indanyl, tetrahydronaphthalene, etc.). The term "alkaryl" as used herein refer to an alkyl that is covalently coupled to an aryl moiety. For example, a benzyl radical is considered an alkaryl under the definition provided herein.

Similarly, the term "alkenyl" as used herein refers to an alkyl in which at least one carbon-carbon bond is a double bond. Thus, the term "lower alkenyl" includes all alkenyls with one to ten carbon atoms. The term "cycloalkenyl" as used herein refers to a cyclic or polycyclic group containing 3 to 15 carbons and at least one double bond. Likewise, the term "alkynyl" as used herein refers to an alkyl or alkenyl in which at least one carbon-carbon bond is a triple bond. Thus, the term "lower alkynyl" includes all alkynyls with one to ten carbon atoms.

As still further used herein, the term "alkoxy" refers to a-OR group, wherein R is lower alkyl, substituted lower alkyl, acyl, aryl, substituted aryl, arylalkyl, substituted arylalkyl, heteroarylalkyl, cycloalkyl, substituted cycloalkyl, cycloheteroalkyl, or substituted cycloheteroalkyl. Similarly, the term "aryloxy" refers to a-OAr group, wherein Ar is an aryl, substituted aryl, heteroaryl, or substituted heteroaryl group.

Furthermore, the term "aryl" refers to an aromatic carbocyclic group having at least one aromatic ring (e.g., phenyl or bipbenyl) or multiple condensed rings in which at least one ring is aromatic, (e.g., 1,2,3,4-tetrahydronaphthyl, naphthyl, anthryl, or phenanthryl). The term "heteroatom" as used herein refers to an atom other than carbon (e.g., S, O, or N), which can optionally be substituted with, e.g., hydrogen, halogen, lower alkyl, alkoxy, lower alkylthio, trifluoromethyl, amino, amido, carboxyl, hydroxyl, aryl, aryloxy, heterocycle, heteroaryl, substituted heteroaryl, nitro, cyano, alkylthio, thiol, sulfamido and the like.

Still further, the term "substituted" as used herein means that a hydrogen atom that is covalently bound to a group or atom (or a free electron pair or electron pair of a double bond of an atom) is replaced by a covalently bound non-hydrogen substituent, including hydroxyl, thiol, alkylthiol, halogen, alkoxy, amino, amido, nitro, carboxyl, cycloalkyl, heterocycle, cycloheteroalkyl, acyl, carboxyl, aryl, aryloxy, heteroaryl, arylalkyl, heteroarylalkyl, alkyl, alkenyl, alknyl, and cyano.

The term "prodrug" as used herein refers to a modification of contemplated compounds, wherein the modified compound exhibits less pharmacological activity (as compared to the modified compound) and wherein the modified compound is converted within a target cell (e.g., neoplastic cell) or target organ (e.g., ovary) back into the modified form. For example, conversion of contemplated compounds into prodrugs may be useful where the active drug is too toxic for safe systemic administration, or where the contemplated compound is poorly absorbed by the digestive tract or other compartment or cell, or where the body breaks down the contemplated compound before reaching its target.

Thus, it should be recognized that the compounds according to the inventive subject matter can be modified in numerous manners, and especially preferred modifications include those that improve one or more pharmacokinetic and/or pharmacodynamic parameter. For example, one or more substituents may be added or replaced to achieve a higher AUC in serum. On the other hand, and especially where increased solubility is desired, hydrophilic groups may be added. Exemplary suitable protocols for conversion of contemplated compounds into the corresponding prodrug form can be found in "Prodrugs (Drugs and the Pharmaceutical Sciences: a Series of Textbooks and Monographs)" by Kenneth B. Sloan (ISBN: 0824786297), and "Hydrolysis in Drug and Prodrug Metabolism: Chemistry, Biochemistry, and Enzymology" by Bernard Testa, Joachim M. Mayer (ISBN: 390639025X), both of which are incorporated by reference herein. Still further, and especially where contemplated compounds have a higher activity when the compound is metabolized (e.g., hydroxylated, glucuronidated, etc.), it should be appreciated that metabolites of contemplated compounds are also expressly contemplated herein.

With respect to suitable kinase inhibitors, and especially BCR-ABL kinase inhibitors it is contemplated that all known kinase inhibitors, but especially BCR-ABL kinase inhibitors are appropriate for use in combination with the compounds according to Formula 1 herein. For example, suitable inhibitors include dasatinib (BMS-354825), nilotinib (AMN107), tyrphostin AG957 (NSC 654705), the adamantyl ester of AG957 (NSC 680410), the selective Abl inhibitor AMN107, and the dual Src/Abl inhibitor BMS-354825. It is generally contemplated that the concentrations of second pharmaceutically active ingredients are typically those recommended for stand-alone administration, however, lower (and in some cases higher) concentrations are also deemed suitable for use herein. Most typically, however, these kinase inhibitors will be administered in dosages and schedules as known for stand-alone administration (or lower where substantial synergistic effect is achieved).

Depending on the particular purpose, it should be recognized that contemplated compounds or combination of compounds may be combined (in vivo or in a pharmaceutical formulation or administration regimen) with further pharmaceutically active ingredients, and especially contemplated other ingredients include DNA damaging agents, cytostatic and/or cytotoxic drugs, antimetabolites, nucleoside analogs, etc. For example, suitable agents include alkylating agents and/or crosslinking agents such as cis-platin, mitomycin, doxorubicin, cyclophosphamide, melphalan, chlorambucil, and/or bleomycin.

It should be particularly appreciated that coadministration of the kinase inhibitor and the compounds according to the inventive subject matter need not be limited to simultaneous administration of both drugs, but may follow numerous protocols so long as both drugs have measurable serum concentration at the same time. For example, the compounds according to Formula I above may be parenterally administered at a dosage of between about 30 mg to 1500 mg, while doses of imatinib of between 400 mg or 600 mg are administered once daily. Therefore, the kinase inhibitor may be administered in one route while the RAD51 inhibitor is administered via a second route. Administration may be performed by the patient (e.g. oral administration) or by a health practitioner as appropriate. Therefore, contemplated pharmaceutical compositions especially include those in which contemplated compounds (and further pharmaceutically active ingredients) are provided with a suitable carrier, wherein contemplated compounds are preferably present at a concentration effective to increase sensitivity of a CML cell to kinase inhibitor treatment. Where contemplated compositions are employed to at least temporarily arrest cells in a cell cycle, it is preferred that the compound is present at a concentration effective to arrest a (typically non-neoplastic) cell in the G1 phase when the cell is contacted with the compound.

Depending on the particular use and structure, it is therefore contemplated that the compounds according to the inventive subject matter are present in the composition in an amount between 1 microgram to 1000 milligram, more typically between 10 microgram to 500 milligram, and most typically between 50 microgram to 500 milligram per single dosage unit. Thus, preferred concentrations of contemplated compounds in vivo or in vitro generally are between 0.1 nM and 500 microM, more typically between 50 nM and 400 microM, and most typically between 100 nM and 200 microM.

Furthermore, it should be recognized that all formulations are deemed suitable for use herein and especially include oral and parenteral formulations. For example, for oral administration, contemplated compositions may be in the form of a tablet, capsule, suspension, or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. However, especially suitable quantities are provided above, and may therefore allow for a daily dose of about 0.001 (or even less) to 100 mg/kg body weight, preferably between about 0.01 and about 50 mg/kg body weight and most preferably from about 0.1 to 20 mg/kg body weight. Typically, a daily dose can be administered in one to four doses per day.

For therapeutic or prophylactic purposes, contemplated compounds are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Among other contemplated uses, it is particularly preferred that the compounds and combination of compounds according to the inventive subject matter can be employed as therapeutic agent in the treatment of neoplastic diseases, and especially CML. In even more preferred aspects, the CML cells are at least partially resistant to treatment with kinase inhibitors such as imatinib at pharmaceutically acceptable doses. However, numerous other diseases are also deemed suitable and may typically be characterized by fast growing neoplastic cells (cell population with relatively high fraction in S-phase). Further contemplated uses of the compounds presented herein include those in which the compounds are employed as research tool to investigate biological functions of Rad51 in its interaction with other Rad51 or non-Rad51 molecules within a cell.

Identification and Synthesis of Compounds Suitable for use Herein

Previous experiments using an inducible reverse yeast two-hybrid method to isolate active compounds from a library of 24,000 synthetic compounds identified among other leads two candidates, IBR1 and IBR2.

Briefly, two fusion proteins, the TetR-BRC fusion protein (TetR/NCB, constitutively expressed) and the Rad51-activation domain fusion protein (AD/Rad51, expressed under the GAL1 promoter), worked together as a transcriptional activator in a yeast strain harboring a TetOp-driven URA3 gene. The interaction between these two fusion proteins induced the expression of URA3 gene, and the toxic metabolite from 5-FOA in the medium caused cell death. If the small molecules tested inhibited TetR/BRC/AD/Rad51 interaction, URA3 expression was abolished and cells are allowed to grow. While screening the library, sixteen compounds were found to promote yeast growth at concentrations below 10 μM. These compounds were then tested for their effects on the IR-induced Rad51 foci formation in MCF-7 breast cancer cells. Two compounds (IBR1 and IBR2) dramatically reduced Rad51 foci formation and were chosen for further investigation. Selected results, synthesis of various compounds, and certain other parameters (e.g., mechanism of binding and selected biological effects) are described in our copending International application with the publication number WO 2006/044933, which is incorporated by reference herein.

Based on these experiments and compounds it is contemplated that numerous IBR analogues with improved efficacy and solubility can be prepared in various synthetic approaches using structure activity (SAR) studies. Most preferably, improved compounds can be prepared using combinatorial synthesis of IBR analogues, synthesis of chiral IBR compounds, alone or in combination with biological function screening. Where appropriate, solubility can be improved by addition of solubilizing moieties, which may be further guided by SAR results. It is thus contemplated that IBR analogues with targeting efficacy against Rad51 can be prepared, which are expected to inactivate Rad51 activity in vitro and/or in vivo. Among other possible desired effects, it is especially contemplated that IBR analogs dissociate Rad51 polymers into monomers and/or inhibit Rad51 in strand-exchange activity. Thus, at least some, or most of contemplated molecules are expected to inactivate Rad51 activity in vivo in CML cells. Still further, Rad51 degradation is expected, which is thought to reduce homologous recombination frequency in CML upon IBR treatment.

Preliminary Structure-Activity Relationship of IBR Analogues

In the initial reverse yeast two-hybrid screening, several compounds in the library share a non-planar hydrophobic common structure with IBR1 and 2. The presence of a phenylsulphonyl group of proper size appears to be essential for successful disruption of the BRCA2-R ad51 interaction. When the phenyl ring was absent (NS16856), or the linker between isoquinoline and phenyl ring was too long (NS7786, NS7787, NS7788, NS34240, and NS40298), or the substituent on phenyl ring is too big (NS35552), the activities of these compounds were negligible as can be seen from FIG. 1A which summarizes compounds in the screened library sharing an indolyl isoquinoline structure. Two compounds, NS7796 (IBR1) and NS7798 (IBR2), were positive in both the yeast two-hybrid screening and IR-induced Rad51 foci formation assay. Two compounds, NS7800 and NS7799, were positive in the yeast two-hybrid screening, but negative in the Rad51 foci formation assay; the remaining compounds were negative in the yeast two-hybrid screening. Remarkably, when the phenyl group was modified into a morpholine, piperidine, or piperizine group, cancer cell growth could not be significantly inhibited at or over 20 mM of corresponding compounds (data not shown). Only relatively minor changes on the phenyl ring (e.g., fluorination) are tolerated, although with a slight decrease of cell growth inhibition activity. In addition, when the indole ring was missing or the N-position of the indole ring was methylated, or tosylated, or alkylated, the cell growth inhibition activity was lost. Moreover, the 2-carboxylation of the indole ring also lost activity.

These findings suggest that the N-position of the indole ring may provide secondary forces to ensure the binding affinity to Rad51 However, 5-bromo or 5-methoxy analogues were able to inhibit cancer cell growth, although with a higher IC50 than IBR2. Therefore, the 5-position of indole ring may provide a potential site for further modification. The inventors also noticed that there is a chiral center in the IBR compounds as marked by an asterisk in FIG. 1B. Initially, the inventors separated these two enantiomers by chiral HPLC (Regis Whelk-O1, Hexane:isopropanol=75:25) as shown in chromatogram of FIG. 1C and determined the absolute configuration by X-ray crystallography. The competitive binding assay suggests there was a roughly 1000 folds difference of these two enantiomers (R vs S) in terms of inhibition of Rad51-BRC repeats binding in vitro as illustrated in FIG. 1D. Here, the inhibition of Rad51-BRC repeat binding was analyzed by SPR in a solution competition format. The median inhibition concentrations of racemic-, S-, and R-IBR2 were about 115 nM, 1000 nM, and 1 nM, respectively.

Based on these preliminary studies, the inventors contemplate the following factors to be significant for IBR activity and to be taken into account in designing various compound libraries: The presence of the phenyl sulphonyl group, the chain length between phenyl and sulphonyl group of less than two, large substitutions on phenyl are not permitted, the presence of an indole ring, N—H of indole moiety is necessary, 5-position of indole can be substituted, and the R-form is more potent than S-form.

Development of IBR Analogues with Improved Efficacy and Solubility

Previously, the inventors identified small compounds targeting Rad51 for proteasome degradation leading to retarded growth of cancer cells. However, the IC50 of these compounds are approximately 10 mM, and these compounds are hardly soluble in aqueous solutions. In order to make these compounds appropriate for practical clinical applications, it is necessary to achieve better affinity as well as better solubility by re-screening newly synthesized IBR analogues.

Combinatorial Synthesis of IBR Analogues

While numerous known combinatorial methods are deemed suitable, it is preferred that a Wang resin is used as a polymer support. Initially, the synthesis is performed at 50-100 mmol levels. The indoles are grafted onto the hydroxy group of the Wang resin through a carbamate linker, which also serves as a protective group for the indolyl NH group against the subsequent coupling reactions. The resulting IBR derivatives can be finally liberated from the resin by trifluoroacetic acid (TFA) or tetra-n-butylammonium fluoride (TBAF) following protocols well known in the art.

Most typically, the key reaction for IBR synthesis is a Reissert-type heteroarylation reaction. Isoquinolines and sulphonyl compounds are first mixed together to form sulphonyl isoquinolium intermediates, which then reacts with the indole resins to form the molecular scaffold. The R1 and R2 substitutions can be introduced by two steps of functional group transformations. For example, the indole and isoquinoline ring with bromine substitution at different positions are used as building blocks, and by Suzuki coupling, properly protected R1 and R2 groups can be introduced at different stages of the syntheses, as exemplarily shown in Scheme 1 below.

Scheme 1

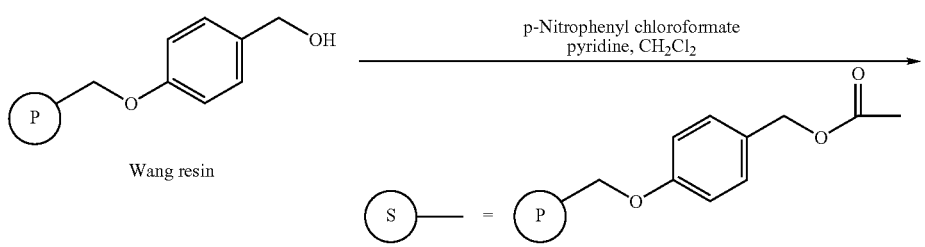

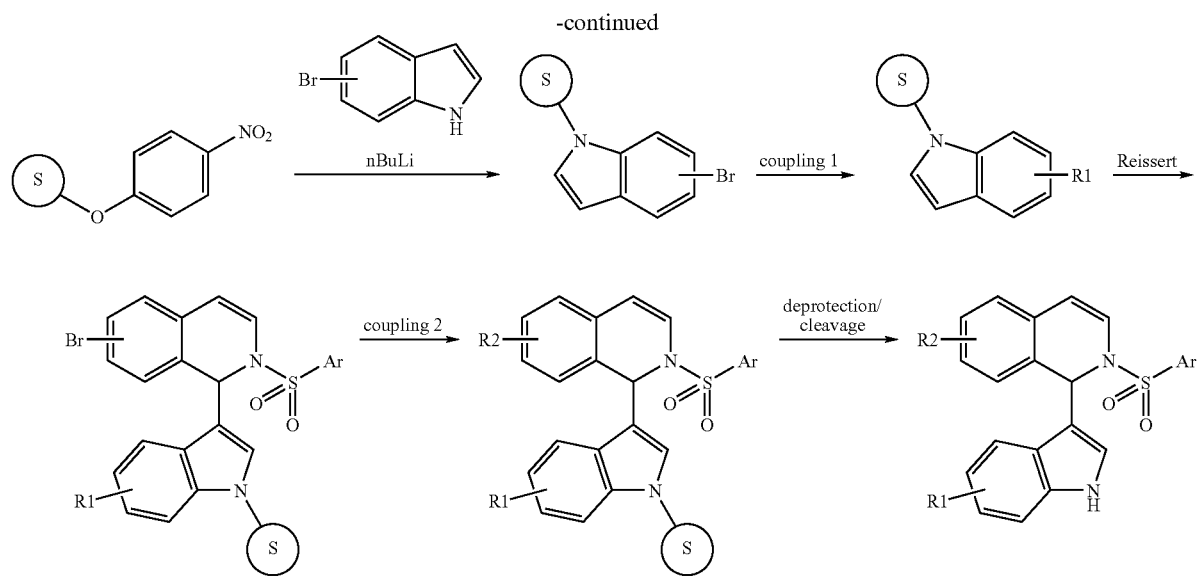

Scheme 1

Proper protective groups for R1 and R2 are chosen such that they can also be removed by TFA or TBAF, to simplify the final deprotection step. After deprotection/cleavage from the resin, the compounds are then purified by HPLC and characterized by LC-MS. If the compound is found desirable, preparative scale synthesis are carried out in solution phase, and full set of structural characterization data are collected accordingly.

Synthesis of Chiral IBR Compounds

As protein is a chiral macromolecule, it can be expected that proteins will present a chiral microenvironment for its ligand. It is therefore conceivable that a pair of enantiomers show differential binding affinity to their target. Indeed, the competitive binding assay of both enantiomers of IBR2 exhibited 1000-fold difference of median inhibition concentration. However, the above two enantiomers only showed 2-3 fold differences in IC50 as determined by MTT assay. This inconsistency between in vitro binding activity and in vivo killing activity may be due to experimental error or different pharmacokinetic properties of both enantiomers. To clarify this inconsistency, considerable amounts of optically pure IBR2 are needed. In addition, developing an asymmetric synthetic methodology of IBR compounds are expected to benefit the entire drug development in the long term.

Scheme 2 summarizes one example of possible asymmetric synthetic routes. In brief, the initial chiral center is introduced by catalytic enantioselective cyanation of o-bromobenz-aldehyde to give the corresponding cyanohydrin, followed by reduction of cyanide and routine protective group operations. The resulting protected o-bromophenyl-a,b-hydroxyl-amine then undergoes a Grignard reaction with protected indole-3-carboxaldehyde to induce the desired chiral center. Then after a couple of group transformations, and an intramolecular ring-closure SN2 substitution, the remaining acid labile protective groups are removed and the resulting compound dehydrated to yield the chiral IBR2 compound.

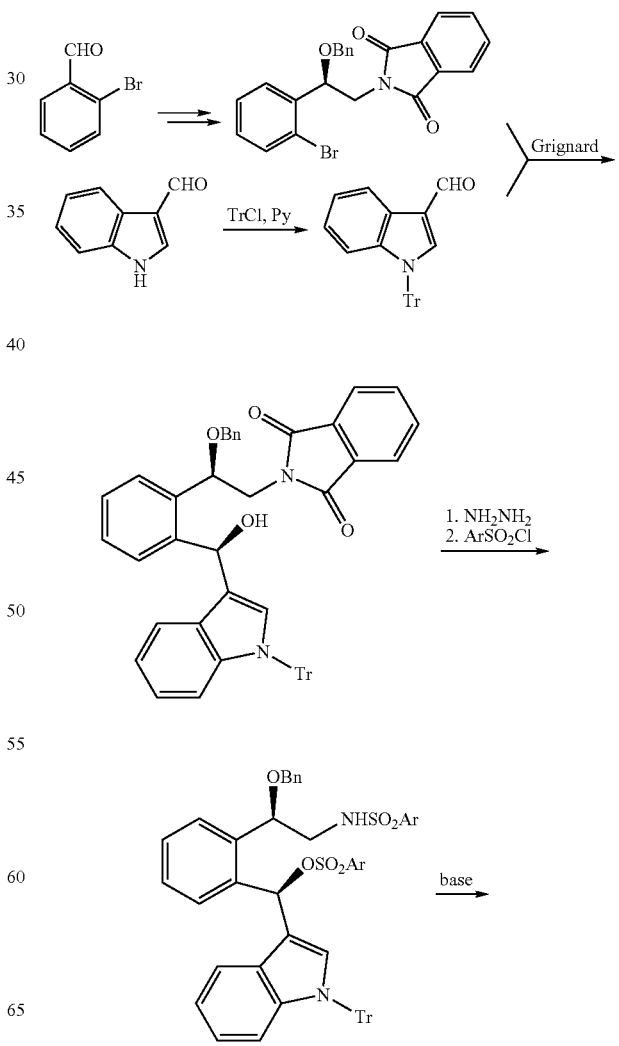

Scheme 2

-continued

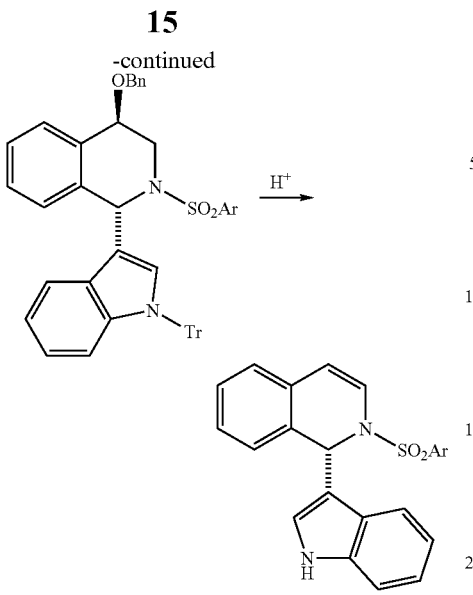

Scheme 2

It should be appreciated that by introducing different substitutions on the starting materials, this method can be expanded to synthesize other chiral IBR analogues as well.

Biological Functional Screening

Newly synthesized compounds are contemplated to be screened using the reverse yeast two-hybrid screening system as described above, and positive hits are revalidated using various established biological functional assays to ascertain that they indeed inhibit cancer cell proliferation and target Rad51 recombinase.

The reverse yeast two-hybrid system is used to perform the second round screening of the modified small compounds. TetR/NCB fission protein which contains BRC1-4 repeats (TetR/NCB) are expressed constitutively; the expression of a RAD51-GAL4 Activation Domain fusion protein (AD/RAD51) is rendered galactose-inducible under GAL1 promoter. Yeast is grown on a galactose medium containing 5-FOA. The assay is performed on 96-well plates. Small molecule compounds are added into the medium at the concentration of 10 mM in the total volume of 100 ml. The compounds that can disrupt the BRC-RAD51 interaction are identified by the viability of the yeast.

Successful chemical entities from the above screening are then verified by cell proliferation assay, and XTT assay. To obtain cell growth curves, $1 \times 10^4$ exponentially growing cells are seeded in 12-well plate for 24 hours. Cells are then treated, in duplicate, with various concentrations (e.g. 0, 1, 5, 10, 20 mM) of compounds in the presence of 0.1% DMSO for one to five days. The viable cells are counted by trypan blue exclusion assay daily. Compounds showing significant inhibition effects on the proliferation of cancer cells is subjected to XTT assay as previously described (Jost et al. 1992) to determine their IC50. Compounds with IC50 less than 10 mM are then subjected to further analysis.

Successful entities are then analyzed with Biacore's surface plasmon resonance (SPR) technique in a solution competition format to determine their median inhibitory concentration on Rad51. Briefly, the assays are performed on a Biacore 3000 (Biacore Inc.) using a Sensor chip NTA (Biacore Inc.) for capturing His-tagged Rad51 protein. The concentration of BRC protein is kept constant. Compounds are dissolved in DMSO at 20 mM and serially diluted in each BRC test sample. The assays are performed at 25° C. in running buffer (10 mM HEPES, 150 mM NaCl, 0.1% DMSO). Relative BRC-Rad51 binding percentage in the presence of inhibitors is calculated. The experiments are carried out in triplicate and averaged. The best-fit competitive binding curve is drawn and median inhibitory concentration of each candidate compound is obtained. The results of these assays are thought to help to establish a quantitative structure-activity relationship, which in turn guides further optimization of the positive hits.

Modification of IBR Compounds to Improve Solubility

In addition to affinity to Rad51, bioavailability issues should be taken into consideration. IBR compounds are very hydrophobic, with calculated log P values of 6-7, and barely soluble in aqueous solutions. This means the initial concentration of IBR compounds in body fluid is very low and most likely these molecules adhere in various membrane structures before they can actually hit the target protein Rad51, which is located in the nucleus. By increasing the aqueous solubility up to two magnitudes, log P is lowered to a more acceptable level. Although pharmaceutical formulation techniques can relieve the current situation to a certain extent, the limitations are inherited from the molecular structure of these compounds. Therefore, it is plausible to build acceptable pharmaceutical properties, such as better aqueous solubility, into the compounds. Because there is no acidic or basic groups on IBR compounds, the idea of directly forming a salt from IBR is likely not applicable in this case. Nevertheless, by covalently attaching a solubilizing side chain onto the compound it is contemplated to convert the compound into a water-soluble one.

Synthesis of IBR Compounds with Solubilizing Moieties

While numerous chemical and physical approaches are conceptually possible, it is generally preferred that either a neutral hydrophilic group, an ionizable organic basic, or an acidic solublizing moiety is employed to increase solubility. First, preliminary data showed that bromo or methoxy substitutions on the 5-position of indole ring retained activity (although with slight increase of IC50 value) suggesting 5-position substitutions may not significantly interfere with the binding pocket. Therefore, the synthesis of these structures is particularly contemplated. Other positions on the indole ring may also be suitable. Furthermore, it is noted that the N-position of the indole ring can be easily modified. However, alkylation or tosylation at this site was proven to be deleterious to activity. Therefore, it is contemplated to modify this site with a removable group, which may be cleaved before it hits the target. For example, IBR2 can be coupled to glucuronic acid by an aromatic self-immulative spacer through a carbamate linker as shown in Scheme 3 below, which has previously been used in making prodrugs for Camptothecin, Fluorouracil, and doxorubicin to improve solubility and reduce toxicity.

Scheme 3

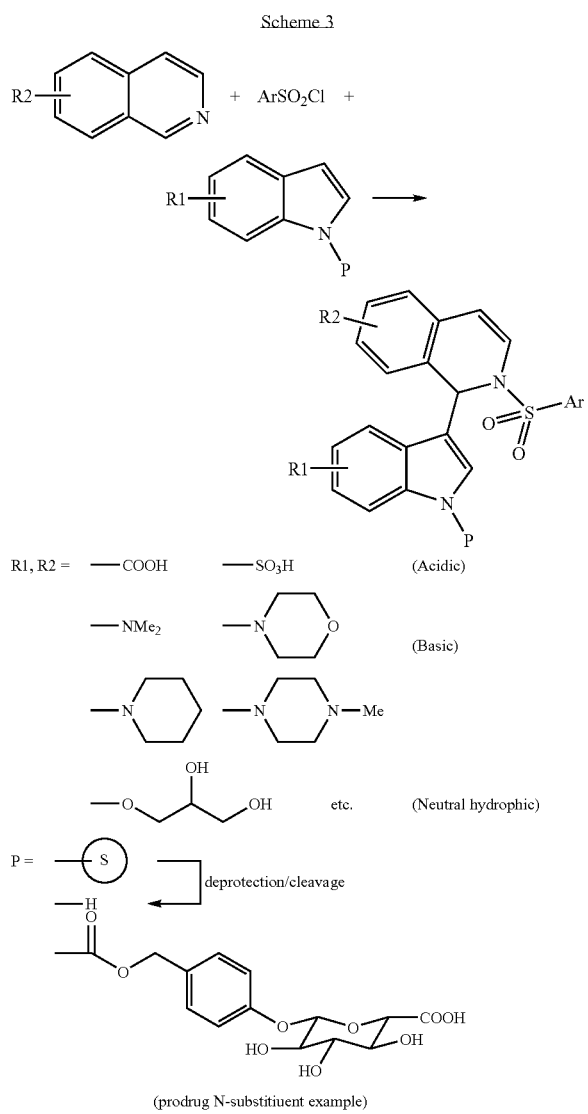

Scheme 3

Alternatively, carboxyl or amino substitutions on the isoquinoline ring may enhance its solubility as well. Finally, a combination of the above substitutions may also be tested. Moreover, as long as there is an acidic or basic group on these modified compounds, salts can be formed with an appropriate counter ion, to improve water solubility. The above-mentioned compounds are synthesized as shown in Scheme 3. Appropriately substituted isoquinolines and indoles are protected first. Indoles are then deprotonated by nBuLi, and attached to the solid support. Isoquinolines are first treated with ArSO2Cl (Ar=Ph or Bn), and then reacted with the indoles on the solid phase. Finally, the beads are treated under suitable deprotection and/or cleavage conditions to furnish the final products. If a removable solubilizing group substitution on the indolyl nitrogen is desired, the reaction is carried out in solution phase, and the cleavage step is not needed. Final products are purified on reverse phase HPLC and molecular weight is verified by LC-MS.

Experiments

Identification of Small Molecules by Reverse Yeast Two Hybrid Screening

To search for small molecules that can mimic BRC repeat to inhibit Rad51 function, the inventors used an inducible reverse yeast two-hybrid method to identify the compounds that disrupt their interactions from a synthetic compounds library as described in WO 2006/044933. While screening the library, several compounds were found to promote yeast growth at concentrations below 10 μM, IBR1 and IBR2. These compounds were then tested for their effects on the IR-induced Rad51 foci formation in MCF-7 breast cancer cells as also described in WO 2006/044933. Two phenylsulfonyl indolyl isoquinolines (IBR1 and IBR2) dramatically reduced Rad51 foci formation. IBR1 and 2 are very similar in molecular structure, suggesting that they share comparable action mechanisms. Particularly, IBR2, which had a slightly stronger activity than IBR1, was characterized in most experiments. An IBR analogue (B6), with a carboxyl group at paraposition of the phenyl ring, was identified as a negative control compound after a systematic study of structure-function relationship of the phenylsulphonyl moiety.

IBR2 Binds to Rad51 and Inhibits its ATP-Dependent Multimerization

To determine whether it was Rad51 or BRC repeat that actually served as a direct target of these compounds, surface plasmon resonance (SPR) was employed to detect the inhibition of protein binding by compound pretreatment. In principle, one of the proteins was attached to the sensor chip, and IBR compounds were allowed to pass through the surface; then, the binding of the second protein was measured. If IBR compounds bind the immobilized protein, the binding of the second protein will be reduced; otherwise, the binding capacity of second protein will be mostly retained. Indeed, upon pretreatment of IBR1 or 2, immobilized Rad51 lost the ability to bind BRC repeat, while the compound pretreatment did not affect the binding of immobilized BRC repeat to Rad51. In contrast, pretreatment of negative compound B6, did not interfere with BRC-Rad51 binding on both chips. These results indicate that IBR compounds target Rad51, rather than BRC repeat.

Figure 2A:
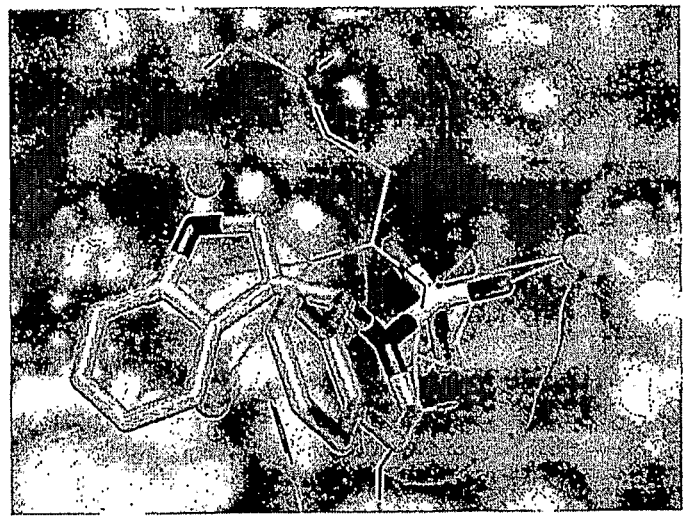
FIG. 2A depicts a simulation of IBR2 binding in the binding pocket on Rad51.

BRC repeats have a highly conserved hairpin structure (e.g., 1524-FHTASGK-1530 in BRC4) that is critically involved in binding to Rad51 core domain through a hydrophobic pocket formed between β-strand B3 and α-helix A4 of Rad51. Molecular docking of IBR2 with Rad51 suggested that IBR2 can extend its phenyl group into the same binding pocket on Rad51 used for BRC binding as depicted in FIG. 2A. Notably, this same binding pocket is also responsible for Rad51 filament formation: Phe1524 of BRC4 or Phe86 of human Rad51 (equivalent to Phe144 in *S. cerevisiae* Rad51, and Phe97 in *P. furiosus* Rad51) can all fit into this pocket. Rad51 multimerization and subsequently filament formation are key functions of Rad51, and these can be inhibited by BRC peptide both in vitro and in vivo. Therefore, if IBR2 mimics the Phe1524 of BRC4 peptide, it is strongly suggested that it also will disrupt Rad51 multimerization as well.

Figure 2B:
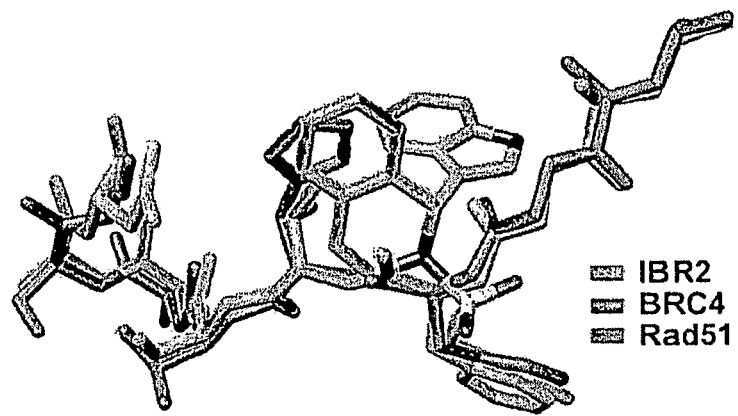
FIG. 2B depicts a structural overlay of IBR2, BRC4, and a portion of Rad51.

To test this possibility, the inventors then compared the gel filtration profile of Rad51 incubated in the presence or absence of IBR2. With IBR2, the Rad51 elution profile exhibited a major peak consistent with the molecular weight of a monomer; while in the presence of the negative compound B6, majority of Rad51 was still able to form multimers (data not shown). These results indicate that IBR2, but not B6, inhibit Rad51 multimerization, suggesting that Rad51-IBR2 binding is specifically through the BRC-binding/multimerization pocket on the Rad51 core domain. The inventors then aligned the 3D structure of IBR2 with the BRC4 hairpin structure and the Rad51 oligomerization motif together. As shown in FIG. 2B, the phenyl ring of IBR2 may mimic Phe1524 of BRC4, as well as the equivalent phenylalanine in Rad51 oligomerization motif. Therefore, one possibility of the action mechanism is that IBR compounds, by mimicking Phe1524 of BRCA2, may block the entrance of the hydrophobic binding pocket on Rad51 core domain, and inhibit BRCA2/Rad51 interaction as well as Rad51 multimerization.

To further determine the binding affinity of IBR2 to Rad51, the inventors then used a Biacore competitive binding assay. IBR2 had an IC50 of 110 nM, while that of B6 was well above 20 μM. Remarkably, the structural modification from a phenyl or benzyl group (as in IBR1 or IBR2) to a p-carboxylphenyl group (as in B6) alone was sufficient to diminish the ability to compete with BRC repeat in Rad51 binding, as well as the ability to inhibit Rad51 multimerization, mainly because the p-carboxylphenyl group of B6 appears to be too large to bind the core domain. These results suggest that IBR2 competitively inhibit BRC-Rad51 binding, and the phenyl moiety plays a key role in the binding.

IBR2 Induces Apoptosis of Ba/F3 Progenitor Cells Expressing BCR-ABL

In CML cells, the constitutively active BCR-ABL is responsible for maintaining high levels of Rad51 activity by direct activation through phosphorylation and transcriptional up-regulation mediated by STAT5. It is therefore contemplated that inhibition of Rad51 activity by IBR2 may have detrimental effects on CML. To test this possibility, murine hematopoietic Ba/F3 progenitor cells expressing different versions of BCR-ABL (e.g., wild-type, T315I, and E255K) mutants were treated with IBR2 at indicated concentrations for 48 hr, and growth inhibition was then determined by XTT (sodium 3'-[1-(phenylaminocarbonyl)-3,4-tetrazolium]-bis (4-methoxy-6-nitro) benzene sulfonate) assay. As shown in FIG. 3A, IBR2 inhibited the proliferation of BCR-ABL-expressing Ba/F3 cells but much less to the Ba/F3 parental cells. Interestingly, the imatinib-resistant T315I mutant was the most sensitive to IBR2 (IC50 12 μM). To further test whether the growth inhibition was resulted from cell death or cytostatic effect of IBR2 treatment, the inventors then determined the percentages of annexin V positive cells, which is indicative of cell death, after IBR2 treatment. As shown in FIGS. 3E and 3F, IBR2 induced apoptosis of Ba/F3 cells expressing WT, T315I or E255K BCR-ABL in a dose dependent manner.

To examine the consequence of the BCR-ABL/Stat5/Rad51 regulatory pathway, the protein expression as well as their phosphorylation states in IBR2-treated cells were analyzed by Western blot. In Ba/F3 cells carrying BCR-ABL expression, dose-dependent decreases of Rad51, BCR-ABL, and phosphrylated Stat5 (p-Stat5) were revealed, while c-Abl, p-c-Abl and total Stat5 protein were unchanged as can be taken from FIG. 3B. On the contrary, there was little effect on Ba/F3 parental cells. The decrease of Rad51 expression in IBR2-treated cells is consistent with the inventors' earlier observation that IBR2 induces Rad51 degradation mediated by proteasome in breast cancer cells. Furthermore, the inventors performed the same set of experiments using compound B6, which has no inhibitory activity to Rad51 in vitro. When treated with compound B6 (up to 100 μM), all four cell lines tested showed no significant reduction in proliferation as can be seen in FIG. 3C and no significant reduction in the BCR-ABL/Stat5/Rad51 protein expression levels as can be taken from FIG. 3D, suggesting that the effects of IBR2 are specific.

IBR2 Synergizes with Imatinib in Induction of Apoptosis in Ba/F3-P210 Cells

Figure 4:
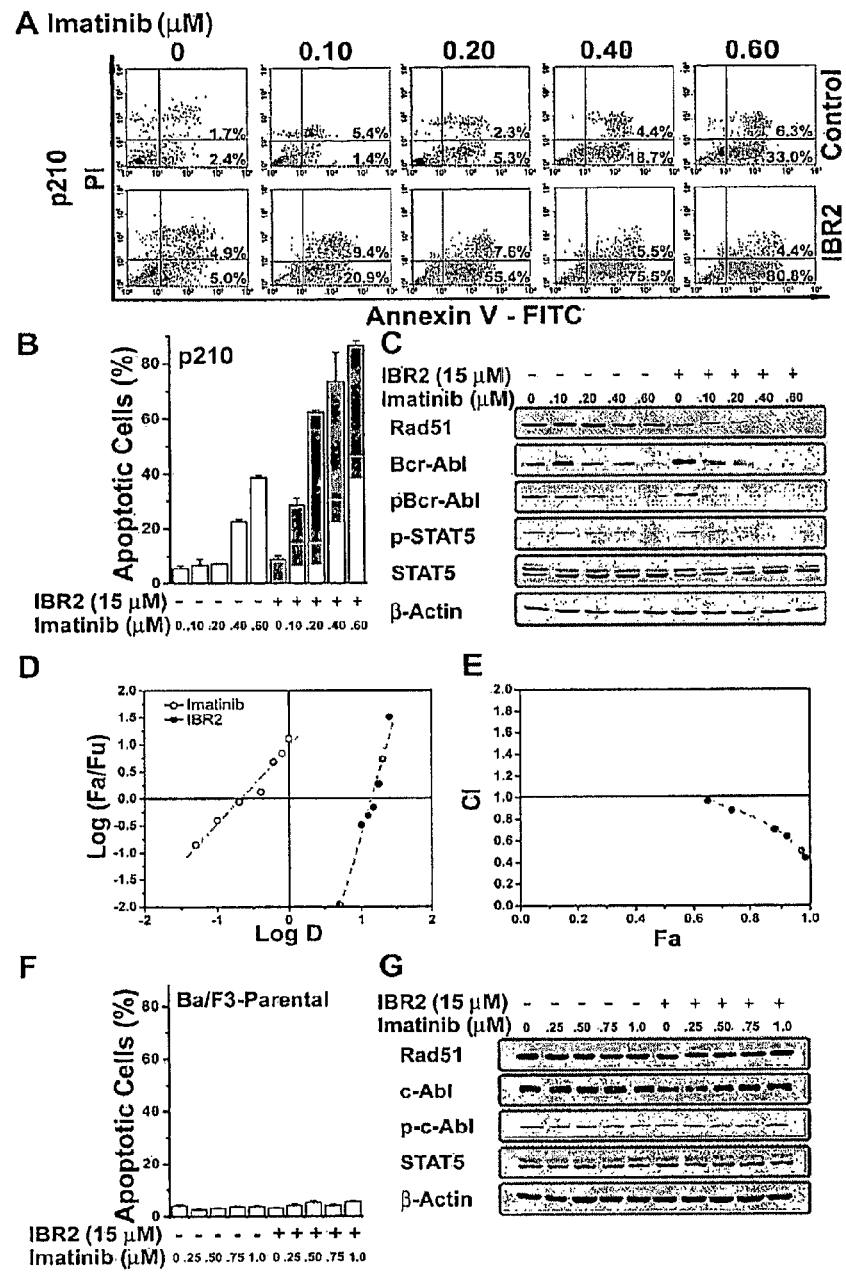
FIG. 4A depicts FACS results of IBR2/imatinib induced apoptosis of Ba/F3-p210 cells in a dose dependent manner.
FIG. 4B is a graphical representation of the results of FIG. 4A.
FIG. 4C depicts Western blots of selected proteins in Ba/F3-p210 cells in the presence of IBR2/imatinib.
FIG. 4D is a graph illustrating median-effect dose and kinetic order of IBR2 and imatinib.
FIG. 4E is a graph illustrating synergistic effect of IBR2 and imatinib.
FIG. 4F is a graph illustrating lack of effect of IBR2 and imatinib on Ba/F3 parental cells.
FIG. 4G depicts Western blots of selected proteins in Ba/F3 parental cells in the presence of IBR2/imatinib.

Since Rad51 and BCR-ABL are in the same pathway essential for cell survival, it was contemplated that simultaneous treatment of Ba/F3-p210 cells with both inhibitors may synergistically enhance the cell death. To assess this possibility, Ba/F3-p210 cells were exposed to various concentrations of imatinib (0 to 0.6 μM) in the presence or absence of IBR2 (15 μM) for 48 hours, after which the percentage of apoptotic cells was determined. Treatment with 15 μM IBR2 alone showed <10% killing effect to these cells, whereas 0.1, 0.2, 0.4 and 0.6 μM imatinib treatment induced apoptosis at about 6.8, 7.6, 23.1 and 39.3%, respectively. Adding IBR2 with imatinib resulted in substantial increases of apoptosis to 28.4, 62.4, 73.6 and 86.4%, respectively, suggesting a synergistic effect. Exemplary results are depicted in FIGS. 4A and 4B.

Figure 5:
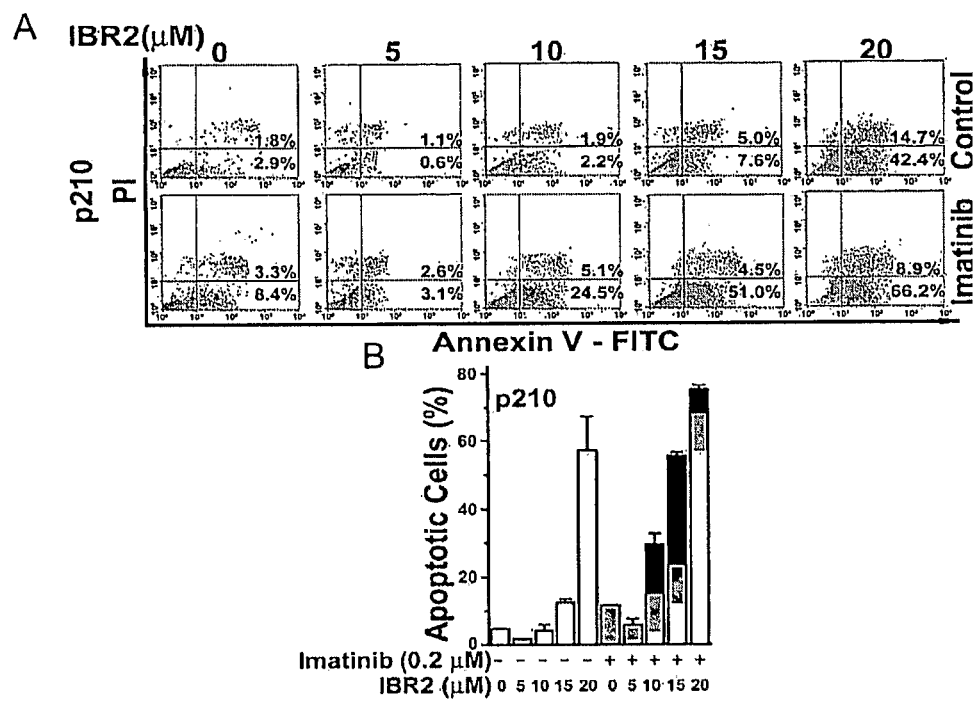
FIG. 5A depicts further FACS results of IBR2/imatinib induced apoptosis of Ba/F3-p210 cells in a dose dependent manner.
FIG. 5B is a graphical representation of the results of FIG. 5A.
Figure 6:
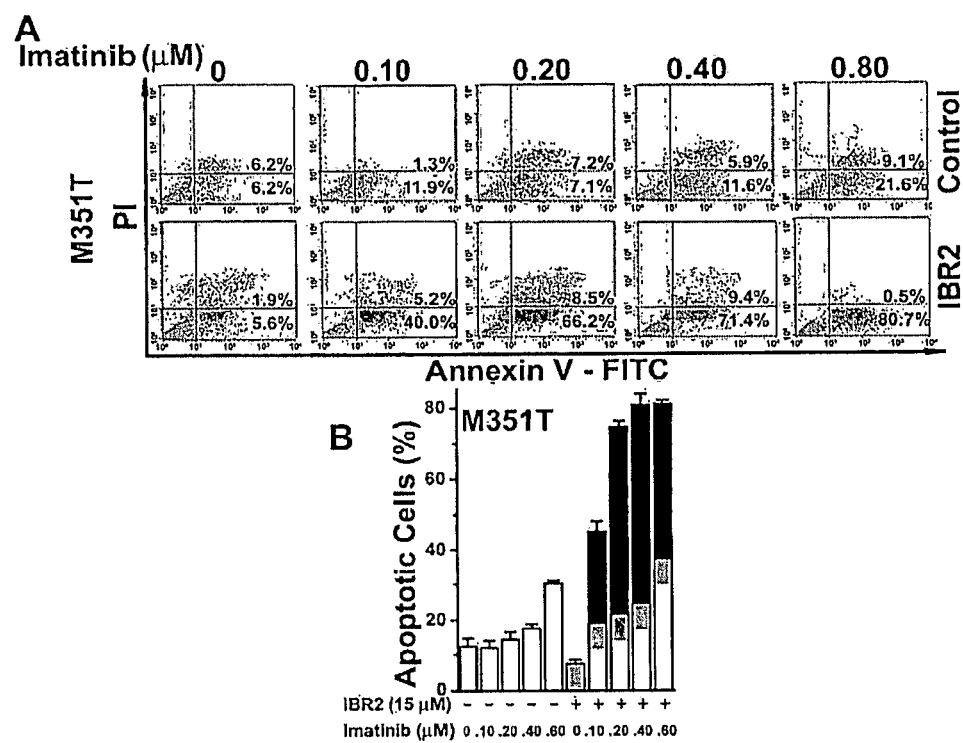
FIG. 6A depicts FACS results of IBR2/imatinib induced apoptosis of Ba/F3-M351T cells in a dose dependent manner.
FIG. 6B is a graphical representation of the results of FIG. 6A.

Reciprocally, Ba/F3-p210 cells were treated with various concentrations of IBR2 (0 to 20 μM) in the presence or absence of imatinib (0.2 μM) for 48 hours and the percentages of apoptotic cells were determined. 0.2 μM imatinib alone showed minimal killing effect to these cells (~10%); whereas 5, 10, 15 and 20 μM IBR2 treatment induced apoptosis at about 1.7, 4.1, 12.6 and 57.1%, respectively. Co-treatment with imatinib-IBR2 resulted in substantial increases of apoptotic percentages, to 5.7, 29.6, 55.5 and 75.1%, respectively (see FIGS. 5A and 5B), supporting the synergistic effect of these two inhibitors to BCR-ABL expressing cells. Similar effects of these two inhibitors were also observed in Ba/F3 cells harboring BCR/ABL M351T mutant, which is modestly imatinib-resistant (see FIG. 6), suggesting the combination treatment may be useful in treating these imatinib-resistant mutants.

To reaffirm that these two inhibitors have a synergistic effect, the inventors first determined the median-effect dose (Dm) and kinetic order (m) of each compound following Chou's method. For imatinib, Dm=0.2 μM, m=1.4; and for IBR2, Dm=13.9 μM, m=4.6 (see FIG. 4D). Based on this, the synergistic effects of the two compounds were revealed by Fa-CI plot, where Fa stands for fraction of cell death, and CI for Combination Index. These results indicate that the combination of IBR2 and imatinib exert a synergistic effect (CI<1) at most data points tested (see FIG. 4E).

The inventors then examined the effects of co-treatment on Rad51, BCR-ABL, and Stat5 protein expression levels as described above. In the absence of IBR2, 0.1-0.6 μM imatinib did not influence the Stat5 protein level, while Rad51, BCR-ABL, p-BCR-ABL and p-Stat5 levels were modestly decreased in a dose-dependent manner as can be seen from FIG. 4C. Whereas in the co-treatment of IBR2 with imatinib, Rad51, BCR-ABL, p-BCR-ABL and p-Stat5 levels were decreased remarkably in a dose-dependent manner, but not on Stat5 protein level (FIG. 4C). These protein expression profiles were concomitantly reflecting the cellular effects.

Figure 7:
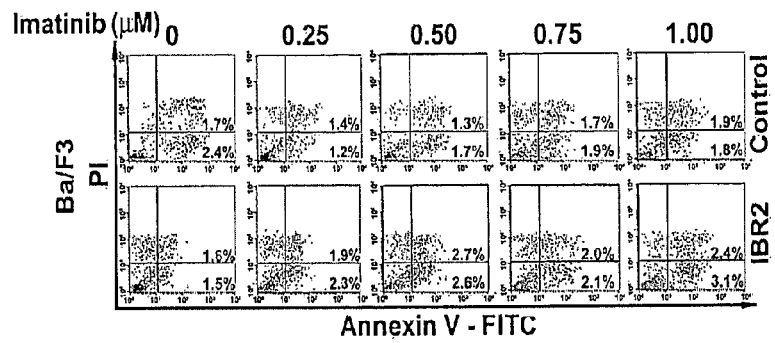
FIG. 7 depicts FACS results of IBR2/imatinib induced apoptosis of Ba/F3 control cells in a dose dependent manner.

As a control, parental Ba/F3 cells were also treated simultaneously with IBR2 and imatinib. Regardless in the absence or presence of IBR2 (15 μM), imatinib (0 to 1.0 μM) did not induce notable cell death (less than 5% apoptotic cells, see FIG. 4F, and FIG. 7. Consistently, protein expression levels of Rad51, c-Abl, p-c-Abl and Stat5 remained rather constant under the treatment (see FIG. 4G). These results suggest that the co-treatment of IBR2 and imatinib had little or none detrimental effect on BCR-ABL negative parental cells.

Figure 3:
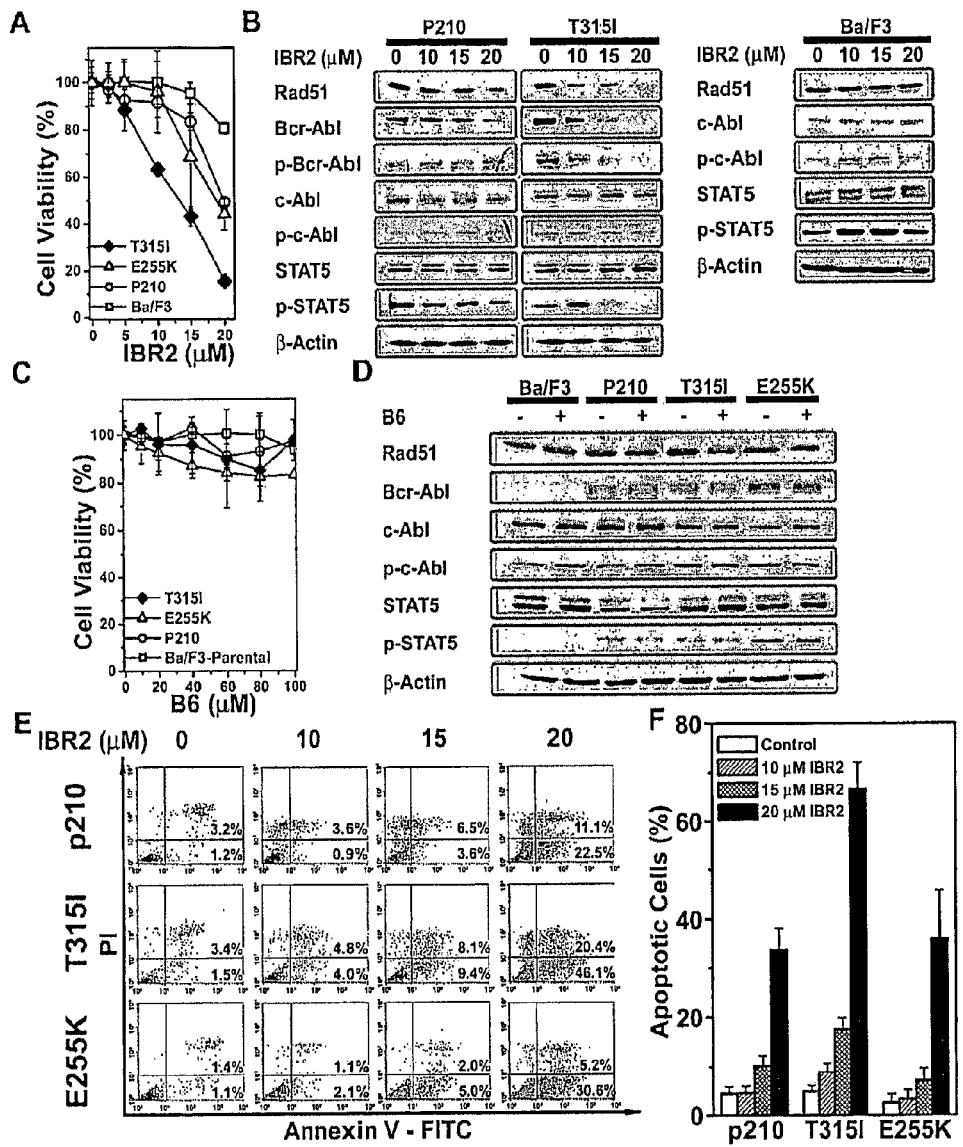
FIG. 3A is a graph illustrating inhibition of proliferation of BCR-ABL-expressing Ba/F3 cells and cells expressing selected BCR-ABL mutants by IBR2.
FIG. 3B depicts Western blots of selected proteins in cells expressing BCR-ABL and mutant forms in the presence of IBR2.
FIG. 3C is a graph illustrating lack of inhibition of proliferation of BCR-ABL-expressing Ba/F3 cells and cells expressing selected BCR-ABL mutants by B6.
FIG. 3D depicts Western blots of selected proteins in cells expressing BCR-ABL and mutant forms in the presence of B6.
FIG. 3E depicts FACS results of IBR2 induced apoptosis of Ba/F3 cells expressing. WT, T315I or E255K BCR-ABL in a dose dependent manner.
FIG. 3F is a graphical representation of the results of FIG. 3E.

IBR2 Induced Cell Death of Imatinib-Resistant Ba/F3-T315I Cells and Prolonged the Lifespan of Mice Bearing Ba/F3-T315I Cells BCR-ABL T315I mutant is very resistant to imatinib and other newly derived compounds including dasatinib (BMS-354825) and nilotinib (AMN107). Direct targeting to Rad51 may provide a potential strategy to overcome this type of resistance. In fact, Ba/F3 cells expressing T315I mutant confers the most sensitivity to IBR2 (FIG. 3). Consistently, 20 µM of IBR2 alone was able to induce over 80% cell death in Ba/F3-T315I cells, while co-treatment with imatinib (up to 4 µM) did not significantly enhance the IBR2-induced killing effect (see FIG. 8A). Next, the inventors examined the effects of IBR2 treatment on the protein expression levels in these cells by western blot. Within 12-24 hours, 20 µM IBR2 alone dramatically reduced the protein expression levels of Rad51, BCR-ABL, p-BCR-ABL and p-Stat5, but not Stat5 (see FIG. 8B). These results suggest that IBR2 alone may be able to inhibit growth of imatinib-resistant CML.

To test whether IBR2 alone can prolong the survival of mice bearing T315I mutant BCR-ABL CML cells, non-Obese Diabetic/Severe-Combined Immunodeficient (NOD/SCID) mice were injected intravenously with Ba/F3-T315I cells and were treated with either IBR2 or imatinib alone for 30 days. Compared with the control group (vehicle alone), imatinib at the dose of 125 mg/kg daily showed no significant improvement in survival of mice (see FIG. 8C, p>0.05). In contrast, the IBR2 (100 mg/kg) treated groups showed significantly prolonged survivals (see FIG. 8D, p<0.01). These results suggest that IBR2 may be effective for treatment of imatinib-resistant CML.

IBR2 Synergizes with Imatinib in Killing Human CML Cell Line K562

Figure 8:
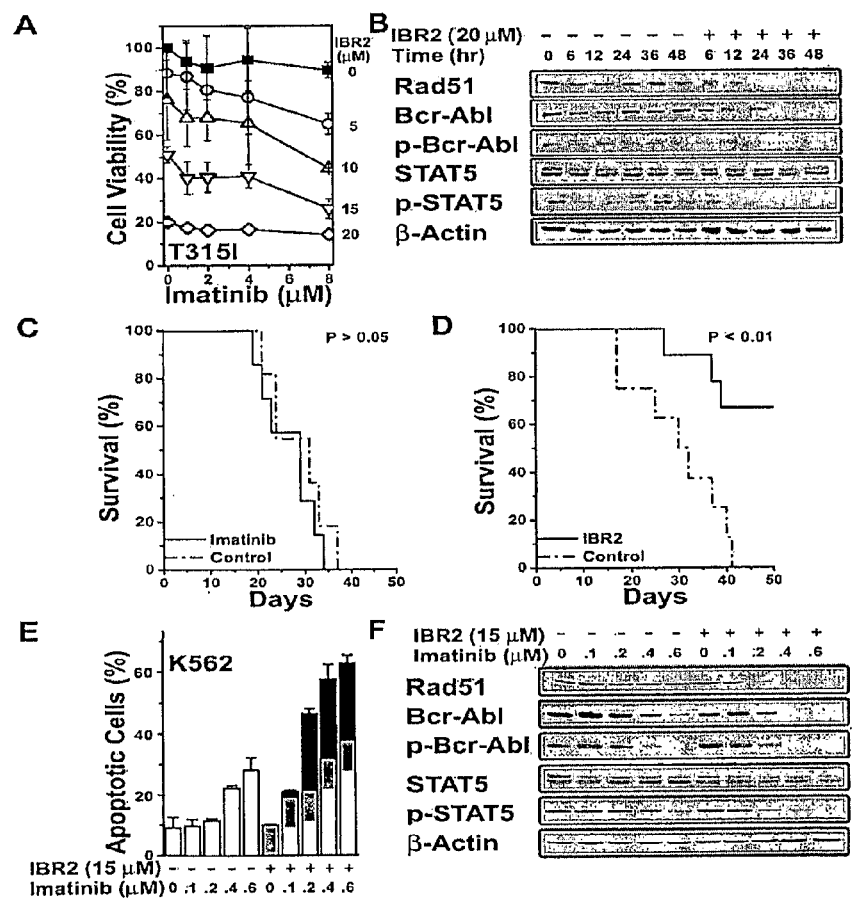
FIG. 8A is a graph illustrating effects of IBR2 alone and IBR2/imatinib on induction of cell death in Ba/F3-T315I cells.
FIG. 8B is a Western blot of selected proteins in Ba/F3-T315I cells treated with IBR2.
FIG. 8C is a graph showing survival rates of imatinib treated (NOD/SCID) mice injected with Ba/F3-T315I cells.
FIG. 8D is a graph showing survival rates of IBR2 treated (NOD/SCID) mice injected with Ba/F3-T315I cells.
FIG. 8E is a graph illustrating increases of apoptotic percentages in IBR2-imatinib treated K562 cells.
FIG. 8F is a Western blot of selected proteins of IBR2-imatinib treated K562 cells.

To test whether IBR2 and imatinib have a similar effect on human blast crisis CML K562 cells, the inventors treated these cells with various concentrations of imatinib (0 to 0.6 µM) in the presence or absence of IBR2 (15 µM) and determined the percentage of apoptotic cells. Treatment of cells with IBR2 alone at 15 µM showed minimal killing effect (apoptotic percentage ~10%); whereas 0.1, 0.2, 0.4 and 0.6 µM imatinib treatment induced apoptosis at about 9.7, 11.8, 22.3 and 28.1%, respectively. Combining IBR2-imatinib treatment resulted in substantial increases of apoptotic percentages, to 21.2, 46.5, 57.5 and 62.6%, respectively (see FIG. 8E). The inventors then examined the protein expression levels of Rad51, BCR-ABL and Stat5 by western blot analysis. In the absence of IBR2, imatinib treatment did not affect Stat5 protein level, while Rad51, BCR-ABL, p-BCR-ABL, p-Stat5 levels decreased in a dose dependent manner (see FIG. 8F). In the presence of 15 µM IBR2, imatinib treatment, significantly decreased the protein levels of Rad51, BCR-ABL, p-BCR-ABL and p-Stat5 in a dose-dependent manner (FIG. 8F). These results suggest that the IBR2-imatinib treatment also has a synergistic effect on human CML cells.

IBR2 Inhibits Proliferation of Both Bcr-Abl Wild Type and Mutant CML Cells

Figure 9:
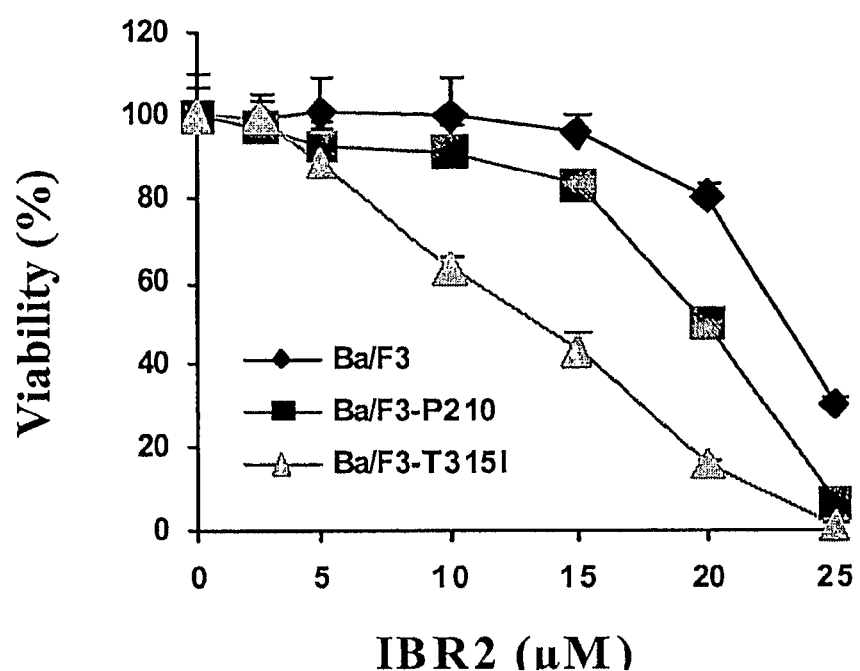
FIG. 9 is a graph illustrating growth inhibition Ba/F3 cells and imatinib resistant CML cell lines Ba/F3-T315I and Ba/F3-T315I Ba/F3-p210 by IBR2.

The inventors also examined the effect of IBR2 on growth of Ba/F3 expressing wild type Bcr-Abl-P210 and Bcr-Abl mutant isoform T315I. Two exponentially growing CML cell lines (Ba/F3-P210 and Ba/F3-T315I) kindly provided by Charles Sawyer (UCLA) were treated with IBR2 at various concentrations (0 to 20 µM) for up to three days; the viable cell numbers were then counted. The results showed that IBR2 significantly inhibited the growth of both CML cancer cell lines in a dose-dependent manner as can be seen in FIG. 9). Interestingly, the Imatinib resistant CML cell line (Ba/F3-T315I), which harbored a T315I mutant isoform of Bcr-Abl tyrosine kinase, exhibited greater sensitivity than wild type Bcr-Abl expressing cell line. FIG. 9 illustrates the effect of IBR2 on parental Ba/F3 cells and Ba/F3 cells expressing WT Bcr-Abl or Bcr-Abl mutant isoform T315I cells. Ba/F3 parental cells and Ba/F3-P210 and Ba/F3-T315I cells were plated in quadruplicate at $5 \times 10^3$ per well, followed by immediate addition of indicated concentrations of IBR2 and/or Imatinib included in the medium. After 72 hours of incubation, proliferation was measured by XTT-based method. Absorbance was measured at 490 nm in a microplate reader. Bars are SD, n=2.

Thus, specific embodiments and applications of RAD51 interfering compositions and methods have been disclosed. It should be apparent, however, to those skilled in the art that many more modifications besides those already described are possible without departing from the inventive concepts herein. The inventive subject matter, therefore, is not to be restricted except in the spirit of the present disclosure. Moreover, in interpreting the specification and claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A pharmaceutical composition for inducing apoptosis in chronic myelogenous leukemia (CML) cells of a patient in need thereof, comprising: a pharmaceutically acceptable carrier in combination with imatinib and a compound of Formula 1A:

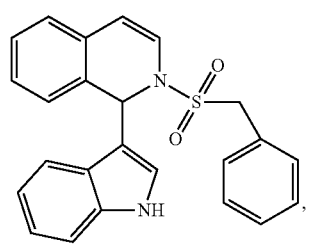

Formula 1A wherein the imatinib and the compound of Formula 1A are present in synergistic amounts with respect to induction of apoptosis in CML cells, and wherein the imatinib and the compound of Formula 1A are present in amounts effective to induce apoptosis in CML cells.

2. A method of treating chronic myelogenous leukemia (CML), comprising administration of the composition of claim 1 to a patient in need thereof.

* * * * *